(12) United States Patent
Jensen

(10) Patent No.: US 8,342,842 B2
(45) Date of Patent: Jan. 1, 2013

(54) DENTAL IMPLANT USING A POLYMERIC POST

(76) Inventor: Steven Jensen, South Jordan, UT (US)

( * ) Notice: Subject to any disclaimer, the term of this patent is extended or adjusted under 35 U.S.C. 154(b) by 0 days.

(21) Appl. No.: 12/823,509

(22) Filed: Jun. 25, 2010

(65) Prior Publication Data

US 2010/0330532 A1    Dec. 30, 2010

Related U.S. Application Data

(60) Provisional application No. 61/220,306, filed on Jun. 25, 2009.

(51) Int. Cl.
*A61C 8/00*    (2006.01)
*A61C 13/12*    (2006.01)

(52) U.S. Cl. ........................................ 433/173; 433/172

(58) Field of Classification Search .......... 433/172–176, 433/201.1, 6, 7, 225, 74; 623/17.17; 403/298, 403/307; 411/510

See application file for complete search history.

(56) References Cited

U.S. PATENT DOCUMENTS

| | | | | |
|---|---|---|---|---|
| 3,849,887 A | * | 11/1974 | Brainin | 433/173 |
| 3,883,258 A | * | 5/1975 | Hewson | 403/298 |
| 4,873,976 A | * | 10/1989 | Schreiber | 606/213 |
| 4,940,355 A | * | 7/1990 | Buchanan | 403/24 |
| 6,186,791 B1 | * | 2/2001 | Karmaker et al. | 433/220 |
| 2003/0153985 A1 | * | 8/2003 | Lee | 623/23.59 |
| 2004/0209228 A1 | * | 10/2004 | Ilan | 433/201.1 |
| 2006/0240385 A1 | * | 10/2006 | Gatti | 433/174 |
| 2007/0031792 A1 | * | 2/2007 | Casement et al. | 433/218 |
| 2007/0141532 A1 | * | 6/2007 | Ford et al. | 433/173 |
| 2007/0190490 A1 | * | 8/2007 | Giorno | 433/173 |

* cited by examiner

*Primary Examiner* — Yogesh Patel

(57) ABSTRACT

The present invention is a dental implant utilizing a polymeric dental post. The actual prosthetic portion of the implant may also be manufactured from a polymer. Various post designs are disclosed for setting and securing the post in a patient's jaw. Numerous polymers are disclosed and may be blended to achieve desired characteristics for both the post and prosthetic.

1 Claim, 2 Drawing Sheets

DENTAL IMPLANT USING A POLYMERIC POST

CROSS-REFERENCE TO RELATED APPLICATIONS

This application claims the benefit of U.S. provisional application Ser. No. 61/220,306, filed Jun. 25, 2009.

TECHNICAL FIELD OF THE INVENTION

The present invention relates to the field of dentistry and more particularly relates to a dental prosthetic implant utilizing a polymer post.

BACKGROUND OF THE INVENTION

Throughout the span of the average individual's life they may through some means lose a tooth. The loss of a tooth may come by many different means such as an accident or decay. The loss of a tooth creates a gap which, on anterior surfaces, may seem aesthetically unpleasant and on a posterior tooth the loss of a chewing surface. The loss of more than one tooth will only exacerbate these problems. Once the tooth is ultimately lost the bone surrounding the tooth begins to deteriorate to the eventual loss of the socket. This creates a number of problems in creating a compatible prosthetic that is capable of replacing a lost tooth. The need for such a replacement tooth brought about the invention of the dental implant.

The dental implant is a device that by design is intended to replace the function of a lost tooth. Commercially available dental implants usually have the following characteristics:

a. Biocompatibility—the material that the implant is made from must be biocompatible. Many materials are not compatible with long-term implantation and are eventually rejected by the body. Therefore, the materials of choice are those that are the most inert—commercially available dental implants have settled upon the metal titanium as the material of choice. Since titanium forms an oxide coating that protects it from further rusting, it is ideal. Other noble metals such as platinum and gold would also be inert, but cost and physical properties would limit their use. Titanium is a good balance between inertness, physical properties, and cost, and is therefore the material most often used.

b. Physical Properties—the material must exhibit sufficient strength and toughness in order to withstand the biting forces present during routine use. A weak biocompatible dental implant would simply break under the constant impact present while biting or chewing. The implant must be durable in that it must survive the constant impact and grinding forces of the teeth over the lifetime of the patient.

Dental implants are usually designed with two pieces. The first one being the post implant and the second being the prosthetic itself. Post implants are designed to be fitted or screwed into the bone, as they are the anchors for the prosthetic. The clinician will usually drill a pilot hole into the bone prior to the insertion of the implant. The implant is then fitted or screwed into the pilot hole and allowed to heal before attaching the finished prosthetic. A clinician has options with respect to bone preparation; in some cases there might be insufficient bone with which to place an implant, therefore the clinician can place artificial bone under the tissue and grow bone if necessary. A clinician can choose the size and type of implant to best fit the patient's needs—if the patient has little bone into which to place an implant a clinician can choose a smaller implant. Though of course there is a trade off with regards to the size of the implant such that smaller implants will be able to withstand less force than a larger diameter implant. Also, the retention of smaller diameter posts within the bone becomes less as the diameter decreases. Therefore, the clinician must carefully choose the correct implant based upon the condition of the patient.

At the end of the post is an abutment or collar to which the prosthetic is attached. The prosthetic is usually created in a lab and usually contains a metal attachment core with a ceramic surface that by design is made to look like a tooth. The finished prosthetic is snapped or connected to the implanted post and the patient at this point has a replacement tooth that is visibly and physically existent.

As to the detailed physical properties of the post implant the intellectual community is divided into two camps. One camp is of the belief that a hard rigid post is superior to a flexible post. The belief being that a rigid post will reinforce the implant and also be more resistant to breakage since it does not undergo repeated flexing. The flexible post implant is argued by some to be superior as it is able to yield under unusual stress and resists being torn out of the socket. There is a need for dental implants whose physical properties can be adjusted for the specific needs of both camps. Metals such as titanium, whose only malleability properties are rigid, cannot fulfill these needs.

The devices and materials of the present invention comprise the use of polymers whose physical properties can be adjusted to precise specifications. These devices comprise both flexible and rigid structures such that unique and custom implants can be produced. The adaptability and flexibility of polymers also allows for improved implant designs where metals would be completely incompatible.

Instead of metals, the devices of the present invention comprise polymers, especially those polymers with exceptional physical properties and inertness. Polymers have advantages over metals in that they have the ability to flex and return to its original shape intact, whereas a metal will usually bend in similar circumstances. Metals are also limited in their method of manufacture in that they must be cast at high temperatures or each piece machined from a block. Polymers on the other hand can be molded at much lower temperatures and in machines that makes their mass production simple. Polymers have the advantage of being able to be compression, injection, blow, or thermoset molded and are generally amenable to other means of molding. Titanium implants are very expensive in part because their manufacture is difficult—e.g., the metal is expensive and the individual milling of each implant is time consuming and costly. The present invention comprises the use of the polymers as a means to create an effective, competitive post at much lower cost and requiring less intensive manual labor.

SUMMARY OF THE INVENTION

In view of the foregoing disadvantages inherent in the known types of dental implants, this invention provides a polymeric dental implant, including a polymeric implant post. As such, the general purpose of the present invention is to provide a new and improved polymeric dental implant that is manufactured to individually desired characteristics of rigidity, flexibility, durability, and other desired characteristics.

To accomplish these objectives, the dental implants of the present invention comprise a polymeric post, the materials from which it is made being selected from the array of known and yet to be discovered polymers to match desired post and prosthetic characteristics.

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views. Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting. As such, those skilled in the art will appreciate that the conception, upon which this disclosure is based, may readily be utilized as a basis for designing other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

Figure 1:
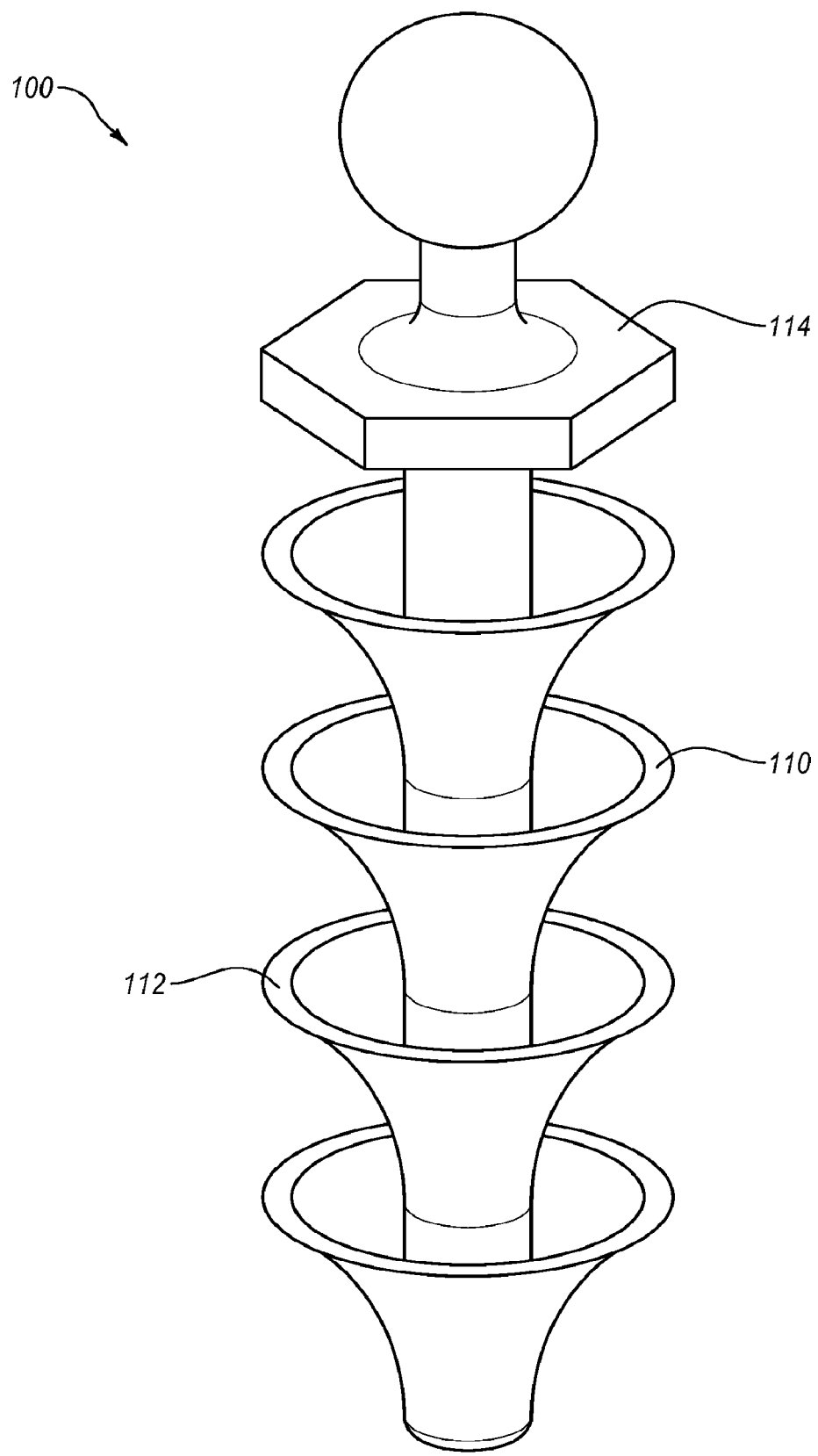
FIG. 1 is a perspective view of a fluted or barbed embodiment of the inventive polymeric implant.

With reference now to the drawings, the preferred embodiment of the polymeric dental implants is herein described. Plastics have an ability to be strong and deform without fracturing under stress. This inherent ability of some polymers to deform (flex/stretch) instead of fracturing is ideal for both an implant post and prosthetic. Plastics that are too brittle can be modified by plasticizers to impart more elasticity to the polymer in order to make them useful as an ideal implant material. Usable plastics can be a thermoplastic or a thermoset plastic. These polymers can be comprised of straight chain, co-polymeric, block or any combination of polymers incorporated into the same mass. Plastics can be chosen from the group of polymers such as: polyacrylates, polyamide-imide, phenolic, nylon, nitrile resins, fluoropolymers, copolyvidones (copovidones), epoxy, melamine-formaldehyde, diallyl phthalate, acetal, coumarone-indene, acrylics, acrylonitrile-butadiene-styrene, alkyds, cellulosics, polybutylene, polycarbonate, polycaprolactones, polyethylene, polyimides, polyphenylene oxide, polypropylene, polystyrene, polyurethanes, polyvinyl acetates, polyvinyl chloride, poly(vinyl alcohol-co ethylene), styrene acrylonitrile, sulfone polymers, saturated or unsaturated polyesters, urea-formaldehyde, or any like or useful plastics. Currently, the preferred plastics of the present invention include: Poly ether ether ketone (PEEK), Hi-lubricity nylons, impact resistant polymethylmethacrylate and fluoro-polymers. These polymers are high strength plastics that are resistant to wear and fracturing. They are also resistant to moisture and chemicals, and are biocompatible. The preferred plastic would also be selected from the group of thermoplastics that are capable of being injection molded, such that the entire implant can be injection molded.

Various polymers can also be modified in order to maximize the warranted characteristics for a dental implant. This usually means incorporating the addition of a plasticizer or filler into the plastic. Plasticizers usually impart more elasticity to the polymer, therefore rendering them more resilient. A few examples of possible plasticizers include: mineral oil, triethyl citrate, acetyltriethyl citrate, lauric acid, modified vegetable oils, diacetylated monoglycerides, castor oil, sucrose diacetate hexaisobutyrate, triacetin, glycerin, liquid polyethylene glycols, liquid poly propylene glycols, propylene glycol, dimethyl phthalate, diethyl phthalate, dipropyl phthlate, dibutyl phthalate, dioctyl phthalate, polysorbates or any like or useful plasticizer.

Fillers can also be incorporated into the plastic. Fillers usually modify the wear resistance, elasticity, fracture toughness and strength of the plastic. Fillers can be comprised of either powder or fiber, such as pieces of monofilament. A few examples of possible fillers would be silica, silica carbide, plastic monofilaments, carbon fiber, zirconia, alumina, borosilicate glass powder, radiopaque borosilicate powder, other radiopaque substances, titanium dioxide, zinc oxide, pigments, or any like or useful filler. Bioactice calcium containing compounds may also be utilized so as to facilitate bone growth and bonding to the surface of the post.

The plastic, filler and plasticizer can be adjusted, for example, in type and relative concentration of the whole to impart essential characteristics to polymers that may be otherwise questionable as a useful dental prosthetic material. Pigments may also be added to the prosthetic in order to manufacture all the shades needed to match the teeth of the human race.

The devices of the present invention can be sold as a complete kit, such that a polymer post is made to fit its custom corresponding polymer prosthetic. The polymer posts can be sold as a kit of many multiple sizes and diameters in order to provide sufficient choice for a variety of patient conditions. These polymer posts of various shapes and sizes would be pre-made by injection, compression, thermoset and any other polymer molding means. Upon selection, the dentist will drill a pilot hole in the bone and fit the implant into the hole by screwing, pressing or other means. Once the polymer post is implanted only the plastic abutment is exposed above the gum line and below the occlusal area in order to provide a protected area that is undisturbed during healing. During the healing interim, the dentist can have fabricated, by either a lab or device, the corresponding prosthetic.

The custom shape of the prosthetic can be acquired by conventional impression material techniques and/or 3D scanning devices with corresponding model manipulation software. Once the design and shape of the post or prosthetic is known, the post or prosthetic can either be sent to a lab for milling and/or rapid prototype manufacture of the final custom post or prosthetic or the milling and/or rapid prototyping of the final post or prosthetic can be done in the dental office, since 3D milling machines are currently available to dental offices and as innovations to the art will tend to favor this option. Eventually, even the rapid prototyping of polymeric posts or prosthetics should become commonplace in a dental office, allowing the creation of a complete polymeric implant. The prosthetic itself may be made of similar polymers as the post, or entirely different ones, again as the practitioner determines need.

In one embodiment, an impression is made of the post or prosthetic and the dimensions of the impression transferred to a numerical database. The dimensions in the database are then used to drive a numerically controlled milling or cutting machine to produce the post or prosthetic. In a second embodiment, an impression is made of the post or prosthetic and the dimensions of the impression transferred to a numerical database. The dimensions in the database are then used to drive a an additive manufacturing process wherein the process machine lays down successive layers of liquid, powder or sheet material to build up a model of the post or prosthetic using a series of thin layers or cross sections, the thin layers or cross sections being fused or joined together to create the final shape of the dental post or prosthetic.

A polymeric post could be comprised of polymers that maximize the physical properties required in a retentive post such as strength and durability, and the prosthetic could be comprised of a different polymer that maximizes the physical properties needed in a prosthetic such as more wear resistance. From the above example it is very evident the increased advantages and options acquired by the devices and materials of the present invention.

The post implant of the present invention can be designed with grooves and/or threads for increased retention. The polymer post can have threads of any size such that the post is intended to be screwed into the bone and gains retention by biting into the bone. Another design contemplates the use of ridges or grooves that are pushed into the pilot hole and merely hold passively until bone can grow around it. One preferred polymeric post is designed with flexible retentive grooves or barbs that flex inward during insertion and resist extraction by flexing outward and biting into the bone under extraction forces. This type of post design would be impossible for a rigid metal; as such metals cannot flex, the corresponding polymeric designs represent an advantage over prior art designs. Said posts are easily inserted and do not require a wrench or other tool to screw them in, they are simply set into place with sufficient force. Said design is superior to a screw type design, a screw type design must bite into the hard and soft tissue where the leading edge must cut into and displace room for an enlarging thread; this cuts and destroys bone in the process and the unattached excess tissue gets pushed between the threads. The body must remove this excess tissue before healing can begin; the flexible groove retentive post of the present invention avoids the cutting and displacement of the screw and minimizes the damage done to the tissues.

The present invention contemplates the use of polymers that expand upon absorption of water such that they expand a surface roughened post into the sides of the bone for retention. Many different designs and methods can be devised with polymeric posts that are within the scope of this patent. In general, all post implant designs that comprise a polymer are within the scope of this patent.

The present invention can be conveniently put together as a complete kit. The kit comprises polymeric posts of varying sizes and shapes to sufficiently cover the various conditions and anatomies of patients. The kit also comprises prosthetic blanks that can be inserted into a 3D milling machine for subsequent custom milling.

Figure 2:
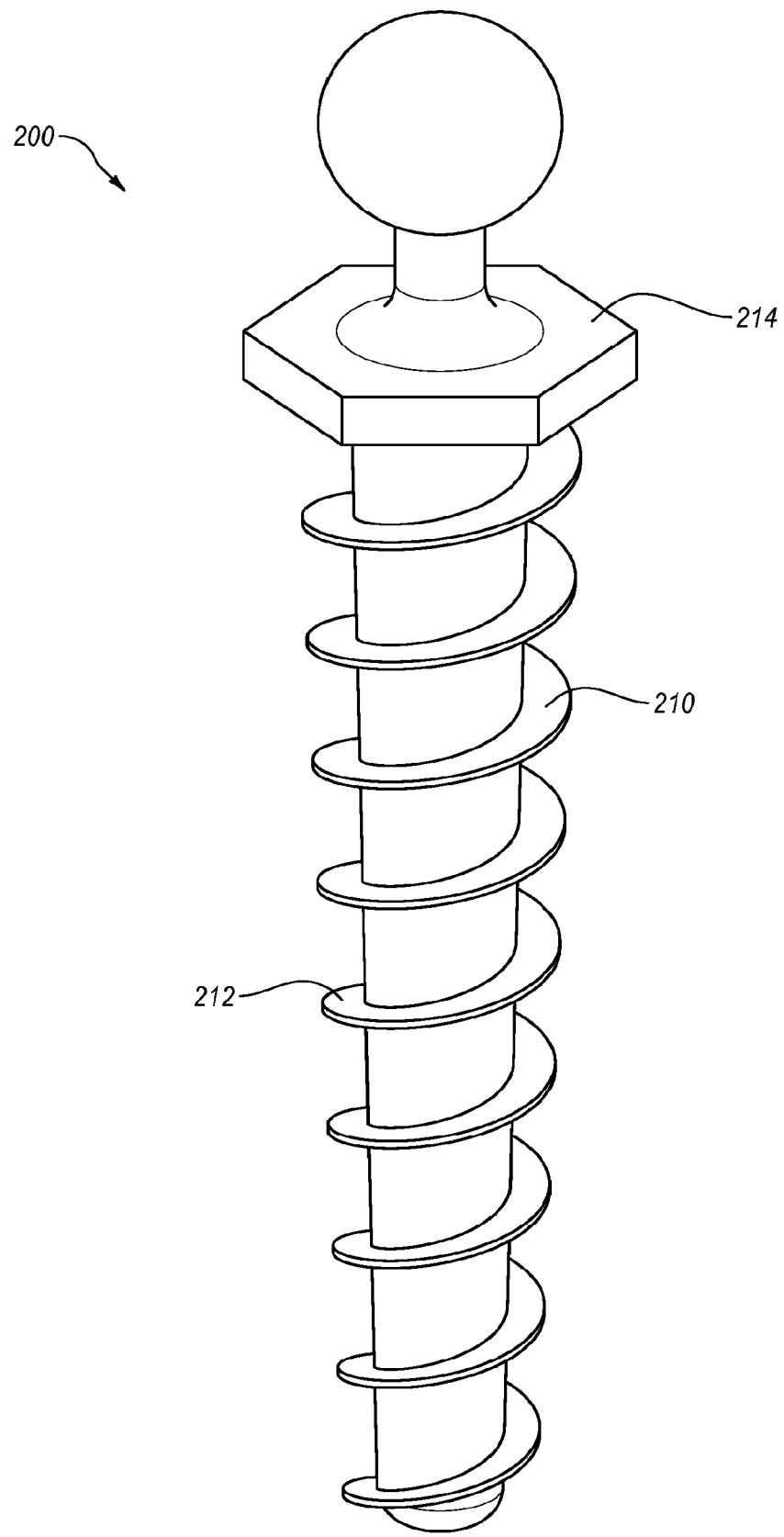
FIG. 2 is a perspective view of a threaded embodiment of the inventive polymeric implant.

Referring now to the drawings, FIG. 1 illustrates a fluted or barbed polymeric implant 100 with flexible retentive grooves or barbs 110 that flex inward during insertion and resist extraction by flexing outward and biting into the bone under extraction forces. In one embodiment, the grooves and barbs include sharp or serrated edges 112 in order to maximize the bite into the corresponding bone for improved retention. FIG. 2 illustrates a screw type polymeric implant 200 having threads 210. In one embodiment, the threads are slightly flexible, allowing them to flex during insertion in order to create a one-size-fits all implant, thereby permitting a screw-type implant of the present invention to be used on multiple sizes of holes or sockets. The threads 210 of the screw type implant 200 are preferably sharp and serrated at the edges 212, permitting engagement with the bone for maximum post-operative retention. In both embodiments, the implant is inserted into the top of the canal and a ratchet is inserted onto the head 114, 214 of the implant wherein the post is screwed or otherwise forced into the canal by twisting with said ratchet while gently applying downward pressure.

Although the present invention has been described with reference to preferred embodiments, numerous modifications and variations can be made and still the result will come within the scope of the invention. No limitation with respect to the specific embodiments disclosed herein is intended or should be inferred.

What is claimed is:

1. A one-piece polymeric dental implant that can be attached to a dental prosthetic, said implant comprising:
   a post portion having a first end and a second end;
   a head that provides a mounting ball for mounting the dental prosthetic located on the first end of the post portion;
   a plurality of flexible and spaced apart barbs extending between the first end and the second end of the post portion, the barbs having a conical configuration surrounding the post and forming conical grooves such that said barbs flex inwardly towards said post during insertion and resist extraction by flexing outward and biting into a bone; and
   a serrated edge on the flexible barbs facing toward the first end of the post portion; and
   a ratchet engaging polygonal portion located between said mounting ball and said barbs.

* * * * *